United States Patent
Zhang et al.

(10) Patent No.: US 9,789,158 B2
(45) Date of Patent: Oct. 17, 2017

(54) APPLICATIONS OF RECOMBINED GANODERMA LUCIDUM IMMUNOREGULATION PROTEIN IN PREPARING DRUGS FOR TREATING TISSUE FIBROSIS

(71) Applicants: Xitian Zhang, Shanghai (CN); Fei Sun, Shanghai (CN)

(72) Inventors: Xitian Zhang, Shanghai (CN); Fei Sun, Shanghai (CN); Chongyang Liang, Shanghai (CN)

(73) Assignees: Xitian Zhang, Shanghai (CN); Fei Sun, Shanghai (CN)

( * ) Notice: Subject to any disclaimer, the term of this patent is extended or adjusted under 35 U.S.C. 154(b) by 0 days.

(21) Appl. No.: 15/101,395

(22) PCT Filed: Jun. 13, 2014

(86) PCT No.: PCT/CN2014/079833
§ 371 (c)(1),
(2) Date: Jun. 2, 2016

(87) PCT Pub. No.: WO2015/120679
PCT Pub. Date: Aug. 20, 2015

(65) Prior Publication Data
US 2016/0303189 A1  Oct. 20, 2016

(30) Foreign Application Priority Data
Feb. 12, 2014 (CN) .......................... 2014 1 0048713

(51) Int. Cl.
| | | |
|---|---|---|
| A61K 49/00 | (2006.01) |
| A61K 39/00 | (2006.01) |
| A61K 45/00 | (2006.01) |
| A61K 38/16 | (2006.01) |
| A61K 36/074 | (2006.01) |

(52) U.S. Cl.
CPC ............. *A61K 38/16* (2013.01); *A61K 36/074* (2013.01)

(58) Field of Classification Search
CPC ............................ A61K 39/00; A61K 39/0002
USPC .................. 424/9.1, 9.2, 184.1, 274.1, 278.1
See application file for complete search history.

(56) References Cited

U.S. PATENT DOCUMENTS

2011/0009597 A1* 1/2011 Sun ........................ C07K 14/37
530/350

FOREIGN PATENT DOCUMENTS

EP  2246064  * 11/2010  ............. A61K 38/16

* cited by examiner

*Primary Examiner* — Rodney P Swartz

(57) ABSTRACT

Applications of recombined *ganoderma lucidum* immunoregulation protein (rLZ-8) in preparing drugs for treating tissue fibrosis are provided.

2 Claims, 2 Drawing Sheets

APPLICATIONS OF RECOMBINED GANODERMA LUCIDUM IMMUNOREGULATION PROTEIN IN PREPARING DRUGS FOR TREATING TISSUE FIBROSIS

CROSS REFERENCE OF RELATED APPLICATION

This is a U.S. National Stage under 35 U.S.C 371 of the International Application PCT/CN2014/079833, filed Jun. 13, 2014, which claims priority under 35 U.S.C. 119(a-d) to CN 201410048713.5, filed Feb. 12, 2014.

BACKGROUND OF THE PRESENT INVENTION

Field of Invention

The present invention relates to an application of recombined *Ganoderma lucidum* immunoregulation protein (rLZ-8) in preparing drugs for treating tissue fibrosis. More particularly, using mice as test subjects, the present invention builds tissue fibrosis models, designs reasonable administration routes and dosage, and regularly testing the fibrosis symptoms of the mice to improve the life quality and prolong the life expectancy of the mice, as well as to evaluate the significance of the recombined *Ganoderma lucidum* immunoregulation protein in preparing drugs for treating tissue fibrosis.

Description of Related Arts

Fibrosis may occur in multiple organs. The main pathological changes of fibrosis include the increase of fibrous connective tissue and the decrease of parenchyma cells, and its continuous progress may lead to structural damage and hypofunction or even failure of organs, posing serious threat to the heath of people.

Body organs consist of two parts: parenchyma and interstitium. The parenchyma refers to the main structural and functional cells of the organs. Distributing between the parenchymal cells, interstitium consists of mesenchyma cells and extracellular matrix and functions as the main mechanical support and connection. In addition, the extracellular matrix rains the micro-environment of cell physiological activities, functions as the bridges of intercellular signal transduction, engages in various physiological and pathological activities, and plays an important part in tissue damage repair and fibrosis.

Take pulmonary fibrosis as an example, as a disease with a high fatality rate, it is receiving more and more attention in the medical profession. Among others, idiopathic pulmonary fibrosis is the most common kind of idiopathic interstitial pneumonia, with an approximate morbidity ratio of 43%-68%. At present, the kinds of pulmonary fibrosis that we discuss most include idiopathic pulmonary fibrosis, pneumosilicosis, allergic alveolitis, pulmonary fibrosis caused by radiation and drugs, and collagen vascular related lung inflammation, as well as various kinds of chronic lung diseases. Besides, a wide variety of chronic and acute lung diseases are often associated with lung inflammation and fibrosis of varying degrees, which are all called interstitial lung diseases. Interstitial lung diseases of different causes all lead to pulmonary interstitial fibrosis, which is the primary factor that causes respiratory failures.

The pathogenesis of pulmonary fibrosis mainly is the inflammatory responses caused by the damage process which involves various inflammatory cells and related media and the excessive deposition of collagen fibers during the fibrosis lung tissue repair process, resulting in the destruction of lung tissue and the loss of normal air exchanging function. The pathologic features of pulmonary fibrosis are the mass concentration of fiber cells turned from pulmonary parenchyma, the excessive deposition of extracellular matrix, accompanied by the inflammation of lungs and tissue structure damage caused by injuries.

Because the pathogenesis of pulmonary fibrosis is not very clear, so there is some difficulty treating it. In the past doctors used nonspecific anti-inflammatory drugs to reduce inflammatory response and alleviate fibrosis; or used glucocorticoids or immunosuppressant to relieve patient symptoms. They failed to treat the roots of fibrosis and the results were not so satisfactory. Usually the course of treatment was accompanied by other complications, or the side effects of some drugs were so serious that they caused damage to other organs, so they failed to improve patients' quality of life. Therefore, the research on new drugs becomes an urgent necessity. At present, after profound study about the nosogenesis of pulmonary fibrosis, people speculate that by blocking the early inflammatory responses or by reducing the excessive deposition of collagen in the repair process, pulmonary fibrosis may be effectively treated, thus various new treatments are formed. Now it is generally acknowledged that the clinical diagnosis and early treatment of pulmonary fibrosis are essential to its treatment. Understanding the Clinical manifestations of pulmonary fibrosis can help confirm the diagnosis earlier and buy precious time for treatment. Research on the ontogenesis of pulmonary fibrosis can help find the best treatment.

In view of the current problem that the drugs for treating tissue fibrosis not only have serious side effects, but also fail to effectively improve the life quality or prolong the lifetime of mice. Therefore, it becomes very important to find drugs that are capable of solving the problems mentioned above. The research is focused on how the recombined *Ganoderma lucidum* immunoregulation protein rLZ-8 be used to prevent and treat drug-induced tissue fibrosis.

SUMMARY OF THE PRESENT INVENTION

The present invention relates to application of recombined *Ganoderma lucidum* immunoregulation protein rLZ-8 in preparing drugs for treating fibrosis. According to the results of a series of experiments, when treating tissue fibrosis, recombined *Ganoderma lucidum* immunoregulation protein has significant pharmacological effects. Compared with other positive control samples, the present invention has significant treatment effect and no side effects. The detailed contents of the invention are as follows:

The present invention uses mice as research subjects, designs and builds different tissue fibrosis models respectively, wherein by using Bleomycin enzymes (BLM) as the drug for modeling to make models and atomization modeling technology, pulmonary fibrosis model of mice is built; by using Doxorubicin (Dox) as the drug to make models and tail intravenous injection method, myocardial fibrosis model of mice is built; by using Cisplatin (CDDP) as the drug to make models of renal fibrosis and intraperitoneal injection method, renal fibrosis model of the mice is built; by using 50% volume fraction carbon tetrachloride solution olive oil as the drug to make models of liver fibrosis and subcutaneous injection method, rats liver fibrosis model is built; By means of contrast experiment, the effect of recombined *Ganoderma lucidum* immunoregulation protein in treating tissue fibrosis is illustrated, the change of tissue fibrosis' biochemical parameters is taken as the main study parameters, and statistical analysis of the experimental results is made by using SPSS statistical software. Statistical results show that there is significant difference between rLZ-8, which has no obvious side effects and other positive drugs in treating tissue fibrosis.

Beneficial effects of the present invention are as follows. The recombined *Ganoderma lucidum* immunoregulation protein (rLZ-8) provided by the present invention has significant effects on treating tissue fibrosis. The present invention uses four typical cases of tissue fibrosis to show that the application of rLZ-8 is apparent in treating tissue fibrosis. In the embodiment of pulmonary fibrosis, compared with positive drugs, the therapeutic effect of rLZ-8 is apparent and advantageous, without accompanying side effects, and capable of prolonging the lifetime of sick mice. In the experiments on heart, kidney and liver, the effect of rLZ-8 is apparent and advantageous. It has positive influence on tissue trauma recovery, fibrosis content and the energy recovery of ALT (U/L), AST (U/L), and ALB (g/L) of the rat model blood serum. At the same time, compared with positive control groups, it was statistically significant. In the middle of some experiments, fibrosis decreases significantly or even disappears in the treatment groups, which is completely unexpected by the inventor and is the best rLZ-8 can do.

DETAILED DESCRIPTION OF THE PREFERRED EMBODIMENT

Figure 1:
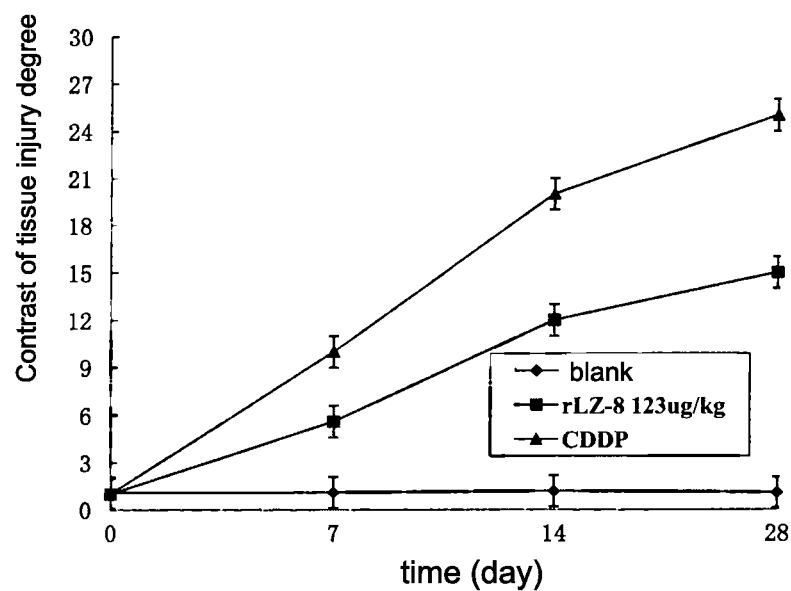
FIG. 1 shows influence of rLZ-8 on tissue injury of renal fibrosis.

Embodiment 1: Model Building of Tissue Fibrosis of Mice

Experiment Materials:
Female Kunming mice with weights ranging from 18-22 g, bleomycin, hydroxyproline kits, propanedione kits, immunohistochemistry kits, antibodies, HE stain reagents, medical atomizing agents, transparent glass containers, conventional reagents such as NaCl, paraformaldehyde, PBS (Phosphate Buffered Saline) etc., anatomical tools, upright fluorescence microscope, mice padding and feed, Real time PCR kit, PCR specific primers, freezing microtome and paraffin slicing machine.

Experimental Method and Operation
Atomization model making, bronchoalveolar lavage techniques, freezing slicing and paraffin slicing technique, HE stain and Masson-trichrome stain technique, ELISA method is used to examine changes of protein in lavage fluid, and streaming method is used to examine the amount of inflammatory cells in lavage fluid.

Modeling Experiment:
1) Modeling experiment grouping: Three groups were classified, a saline group (group A), a low BLM dose group (group B 4 mg/mL), a high BLM dose group (group C 8 mg/Ml), there were 12 mice in each group. The 12 mice in each group were divided into two groups, with 6 mice in each group and the two groups of mice were respectively put into 20×20×20 cm transparent glass containers with corresponding marks, then saline and BLM was sprayed respectively into the containers with medical ultrasonic nebulizers.

2) Model administration process: Each time the spray volume was 1 ml, then a glass cover was closed for 15 minutes and the mice were put back into cages to rest for 5 minutes, and the procedure was repeated 6 times.

3) Examination of the experimental results: death conditions of the mice were recorded every day at 9 o'clock and 17 o'clock and activities thereof were closely watched. The mice were killed respectively after 3 days, 7 days, 14 days and 21 days of feeding, and the lungs of the mice were taken out to see changes in appearance, color and the lung surface; after the lungs were taken out, broncho-alveolar lavage was done first, and then parts of the lung tissue were sliced into paraffin sections and histological examination was done on HE stain; RT-PCR was done on another parts of lung tissue to examine RNA level. Judged from histological analysis, RNA level, protein level and changes in amounts of inflammatory cells, a decision was made to see whether the model of pulmonary fibrosis is usable. The table below is the grading standards made by method of Szapiel to evaluate grading standard of seriousness of the pathological changes in the lung tissue.

TABLE 1

Szapiel grades of pathological changes in lung tissue

| Grades of pathological changes | Seriousness | Affected area of lung tissue |
| --- | --- | --- |
| 0 | no alveolitis or fibrosis | 0 |
| I | mild alveolitis or fibrosis | <20% |
| II | medium alveolitis or fibrosis | 20%-50% |
| III | severe alveolitis or fibrosis | >50% |

There are 4 grades in Szapiel's pathological changes in lung tissue: "0" is grade 1; "I" is grade 2; "II" is grade 3; and "III" is grade 4. The higher the grade, the severer the degree of fibrosis is.

Conclusions of the Experiments:
Research on influences of fibrosis pathological grades of BLM induced mice by modeling dosages: on the 21 day, in the saline group, alveolar structures of the mice were intact, the alveolar wall was rather thin, and there was no extracellular matrix deposition around the external periphery of the alveolar wall and no exudation of inflammatory cells; in the low BLM dose group, alveolar structures of the mice were partly damaged, with small amount of extracellular matrix deposition around the outer periphery of the alveolar wall and small amount of exudation of inflammatory cells; in the high BLM dose group, lung tissue structures of the mice were severely damaged, with large amount of extracellular matrix deposition around the outer periphery of the alveolar wall and large amount of exudation of inflammatory cells, and there were almost no intact alveolar structures as shown in FIG. 1. The lung tissue was paraffin sectioned and HE stained, graded according to Szapiel grade standards, the tissue fibrosis degrees were recorded; the results showed that in the saline group, there were almost no fibrosis areas in sections of the mice, in the low BLM dose group, 66% of lung sections of the mice showed medium fibrosis, and in the high BLM dose group, 75% of the lung sections of the mice showed severe fibrosis. Lung tissue in the saline group showed no fibrosis pathological changes; when making BLM atomization models, in the low BLM dose group, most parts of lung tissue of the mice showed medium fibrosis, part of the lung tissue was healthy and was able to survive; in the high BLM dose group, the majority of lung tissue of the mice showed severe fibrosis, and most of them died of respiratory failures, making it impossible to do the follow-up treatment experiments. Therefore, when doing drug treatment, low BLM dose was chosen to make the models.

TABLE 2

The results of modeling experiment and Szapiel grade standards classification thereof

| Experiment groups | n | 0 | I | II | III |
|---|---|---|---|---|---|
| Saline group | 12 | 12 | 0 | 0 | 0 |
| Low BLM group | 12 | 0 | 3 | 8 | 1 |
| High BLM group | 12 | 0 | 1 | 2 | 9 |

Classified by Szapiel grade standards, in the saline group the lung tissue sections were all normal; in the low BLM dose group, pulmonary fibrosis was mostly medium; in the high BLM dose group, pulmonary fibrosis was mostly severe.

Embodiment 2 the Effect of rLZ-8 on Pulmonary Fibrosis of Mice

Experiment Groups:

there were 7 groups in the experiment and 12 mice in each group. The groups were a saline group (group A), a model group (group B), a low treatment dose group (group C), a medium dose group (group D), a high dose group (group E), a positive control group (group F) and an administration group one week after modeling (group G). The process of modeling was the same as the embodiment 1.

Treating Process:

groups B, C, D, E, F and G all adopted low BLM dose for modeling. Group A and Group B were injected with saline for serving as contrast groups; Groups C, D and E were injected with rLZ-8 each day for treatment. Mice in these groups were weighed every 3 days and drugs were administrated according to weights of the mice. The dose for Group C was 3.84375 μg/kg, the dose for Group D was 7.6875 μg/kg, the dose for Group E was 19.21875 μg/kg, Group F were injected with positive drug dexamethasone 4 mg/kg, Group G were injected with rLZ-8 for treatment 1 week after modeling and the dose was 7.6875 μg/kg.

Experiment Records:

The physiological indexes and deaths of the mice were recorded every day at 9 o'clock and 17 o'clock. On the 14$^{th}$ day and the 21$^{st}$ day, 6 mice were randomly picked and killed in each group. Lungs of the mice were taken out to watch the color of the lungs, if the surface was intact or not, and the changes in the lung surface; parts of the lung tissue were paraffin sectioned and HE stained to be examined histologically; other parts were done with RT-PCR to examine the RNA level. According to histological analysis, RNA level, protein level and the change in the amount of inflammatory cells, the grades of fibrosis were decided.

Experimental Results:

Lung tissue was paraffin sectioned and HE stained to decide its fibrosis grade. In the saline group, lung tissue of the mice showed no fibrosis; in the model group, the lung tissue of the mice mostly showed medium fibrosis; in group D, the fibrosis grade was mostly recovered to mild fibrosis; however, in group C the grade of lung tissue fibrosis was mostly medium, some parts showed mild fibrosis; but in group E, the grades of pulmonary fibrosis were similar, mostly mild and medium; in the positive control group (group F), the grades of pulmonary fibrosis were mostly medium, with some of them showing grades mild or severe. The detailed statistics were given in Table 3.

TABLE 3 rLZ-8 inhibited BLM-induced pulmonary fibrosis

| Experiment groups | n | 0 | I | II | III |
|---|---|---|---|---|---|
| Group A | 12 | 12 | 0 | 0 | 0 |
| Group B | 12 | 0 | 1 | 7 | 4 |
| Group C | 12 | 1 | 3 | 4 | 4 |
| Group D | 12 | 3 | 2 | 6 | 1 |
| Group E | 12 | 2 | 4 | 4 | 2 |
| Group F | 12 | 0 | 3 | 5 | 4 |
| Group G | 12 | 1 | 3 | 6 | 2 |

Seen from the experimental results, compared with positive control group (group F), medium rLZ-8 dose groups (group D and group G) showed obvious efficacy. First of all, in terms of severe fibrosis, it showed that rLZ-8 enables lung tissue to actively recover to medium pulmonary fibrosis; compared with group F, it can be seen that the number of mice with severe fibrosis was significantly reduced; in terms of the absence of fibrosis, compared with positive control group (group F), medium rLZ-8 dose group (group D and group G) showed a clear advantage, during the treatment period, some cases were partly cured; but in the positive control group (group F), no cured cases were observed.

Embodiment 3 the Establishment of the Mice Myocardial Fibrosis Models 100 female Kunming mice weighed 18-22 g were picked and divided into 5 groups: saline group, model group 1 (Dox 1 mg/kg), model group 2 (Dox 2 mg/kg), model group 3 (Dox 3 mg/kg) model group 4 (Dox 4 mg/kg), the number of mice in each group were 15, 15, 25, 30 and 15. Twice a week, every mouse was injected 2000 every time, in which 1 mg/kg Dox, 2 mg/kg Dox, 3 mg/kg Dox or 4 mg/kg Dox was dissolved.

The activities of the mice were closely watched and deaths of the mice were recorded every day at 5:00 pm and 9:00 am. Three days, the 35$^{th}$ the 42$^{nd}$ and the 49$^{th}$ day were chosen to take samples. After deaths, hearts of the mice were taken and rinsed with cold PBS and placed on a clean dry filter paper, then they were put into paraformaldehyde solution to be fixed. The models to assess myocardial fibrosis were established according to histological analysis, the changes in ventricular cavity of the mice, perivascular fibrosis, interstitial fibrosis, and vacuole formation and other changes were taken into consideration to determine whether the model was useable.

TABLE 4

J.P. Bertinchant etc. myocardial fibrosis grades standards:

| | Lesion classification | | | |
|---|---|---|---|---|
| Lesion area | 0 | + | ++ | +++ |
| Perivascular fibrosis | No lesions | Rather Mild fibrosis | Mild fibrosis | Moderate fibrosis |
| Interstitial fibrosis | No lesions | Rather Mild fibrosis | Mild fibrosis | Moderate fibrosis |
| Myocardial tissue vacuolization | No lesions | Rather Mild fibrosis | Mild fibrosis | Moderate fibrosis |

Experimental Results:

As shown in Table 5, it can be seen from the Table that with the extension of time for modeling, in myocardial tissue of the mice, perivascular fibrosis, interstitial fibrosis and vacuolization among tissue increased gradually, and when the dose cumulated to 42 mg when making models, namely after given 3 mg/kg Dox intraperitoneal injection twice a week, in the seventh week the mice showed rather obvious myocardial fibrosis. Besides, with this model making method, mortality rate of the mice was relatively low, so it was conducive to establish stable myocardial fibrosis model of the mice. These results suggested that Dox increased myocardial injury in mice, and with the extension of time for modeling, the severity increased. The most appropriate dose for modeling was 42 mg, namely twice a week 3 mg/kg Dox intraperitoneal injection for 7 weeks.

TABLE 5

Histological changes after Doxorubicin or saline treatment

| | | Histological Damage | | | | | | | | | | | |
|---|---|---|---|---|---|---|---|---|---|---|---|---|---|
| Accumulated Dose | Number of Mice | Perivascular Fibrosis | | | | Interstitial Fibrosis | | | | Vacuolization | | | | Number of deaths |
| | | 0 | + | ++ | +++ | 0 | + | ++ | +++ | 0 | + | ++ | +++ | |
| 30 | 10 | 7 | 3 | 0 | 0 | 9 | 1 | 0 | 0 | 10 | 0 | 0 | 0 | 0 |
| 36 | 10 | 7 | 2 | 1 | 0 | 10 | 0 | 0 | 0 | 9 | 1 | 0 | 0 | 0 |
| 42 | 9 | 4 | 2 | 2 | 1 | 5 | 1 | 2 | 1 | 4 | 2 | 2 | 1 | 0 |

Embodiment 4 the Treatment Effect of rLZ-8 on Dox Induced Mice Myocardial Damage Experiment Grouping:

There were 8 experimental groups, 10 mice/per group, saline group (Group A), model group (Group B), rLZ-8 3 μg/kg (Group C), rLZ-8 6 μg/kg (Group D), rLZ-8 12 μg/kg (Group E), rLZ-8 24 μg/kg (Group F), rLZ-8 48 μg/kg (Group G) and positive control group (Group H).

Treating Process:

The model making process was the same as embodiment 3. The models for groups B, C, D, E, F, G and H were made with 3 mg/kg Dox, and then as control groups, Groups A and B were given intraperitoneal injection of saline once every day, and Groups C, D, E, G and H were treated with rLZ-8, intravenous injection once every 2 days. The mice were weighed every 3 days and drugs were delivered in accordance with weights. The dose for Group C was 3 μg/kg, Group D was 6 μg/kg, Group E was 12 μg/kg, Group F was 24 μg/kg, Group G was 48 μg/kg, and as the positive control group, every two days the mice in Group H were given 10 mg/kg fosinopril sodium tablets by way of intragastric administration.

Experiment Records:

The deaths of the mice were recorded at 9:00 and 17:00 every day and activities of the mice were closely watched. By the $7^{th}$ week, the mice were killed and hearts of the mice were taken out and rinsed with cold PBS, placed on a clean dry filter paper and then were put into paraformaldehyde solution to be fixed. The myocardial tissues were made into paraffin sections and were treated with HE staining and trichrome staining to do histological examinations.

Experimental Results:

In order to examine myocardial fibrosis grades of the mice and myocardial fibrosis status, in the seventh week, samples were taken according to the mortality rates. As shown in Table 6, from the negative control group to the positive control group, in each group the number of mice was 10, 2, 1, 4, 6, 6, 8 and 7 respectively. Sample taking: the mice were killed with the right amount of anesthetic injections and hearts of the mice were isolated under sterile conditions and rinsed with cold PBS, and then blood was blotted up filter paper. The ventricles were selected and crosscut at a ½ section. The myocardial tissue was put into 4% paraformaldehyde solution to be fixed, then it was paraffin sectioned and HE stained. Three slices were cut from each tissue and stained under the same conditions. The myocardial tissue of the mice was Masson stained and was photographed under 20 times 40 times microscopes and statistics were recorded. Results: in the negative control group, one out of ten mice showed + grade perivascular fibrosis; the mice in the model group showed rather serious interstitial fibrosis and vacuolization; In the low dose groups rLZ-8 3 μg/kg and rLZ-8 6 μg/kg, interstitial fibrosis and vacuolization were observed, but with the increase of the dose, the myocardial fibrosis indexes of the mice gradually weakened; when the dose increased to rLZ-8 48 μg/kg, only two mice showed + grade perivascular fibrosis and + grade interstitial fibrosis; in the positive control group, one out of 7 mice showed + grade perivascular fibrosis and + grade interstitial fibrosis, and another one showed ++ grade perivascular fibrosis and ++ grade interstitial fibrosis.

TABLE 6

Treating effect of rLZ-8 on Dox-induced myocardial damage in mice

| | | Histological Damage | | | | | | | | | | | |
|---|---|---|---|---|---|---|---|---|---|---|---|---|---|
| Groups | Number of Mice | Perivascular Fibrosis | | | | Interstitial Fibrosis | | | | Vacuolization | | | | Deaths |
| | | 0 | + | ++ | +++ | 0 | + | ++ | +++ | 0 | + | ++ | +++ | |
| Group A | 10 | 9 | 1 | 0 | 0 | 10 | 0 | 0 | 0 | 10 | 0 | 0 | 0 | 0 |
| Group B | 2 | 0 | 0 | 0 | 2 | 0 | 0 | 2 | 0 | 0 | 1 | 1 | 0 | 0 |

TABLE 6-continued

Treating effect of rLZ-8 on Dox-induced myocardial damage in mice

| Groups | Number of Mice | Perivascular Fibrosis | | | | Interstitial Fibrosis | | | | Vacuolization | | | | Deaths |
|---|---|---|---|---|---|---|---|---|---|---|---|---|---|---|
| | | 0 | + | ++ | +++ | 0 | + | ++ | +++ | 0 | + | ++ | +++ | |
| Group C | 1 | 0 | 0 | 0 | 1 | 0 | 0 | 0 | 1 | 0 | 0 | 1 | 0 | 0 |
| Group D | 4 | 0 | 0 | 2 | 2 | 0 | 0 | 3 | 1 | 3 | 1 | 0 | 0 | 0 |
| Group E | 6 | 4 | 2 | 0 | 0 | 3 | 3 | 0 | 0 | 5 | 1 | 0 | 0 | 0 |
| Group F | 6 | 5 | 1 | 0 | 0 | 4 | 2 | 0 | 0 | 6 | 0 | 0 | 0 | 0 |
| Group G | 8 | 7 | 1 | 0 | 0 | 7 | 1 | 0 | 0 | 8 | 0 | 0 | 0 | 0 |
| Group H | 7 | 5 | 1 | 1 | 0 | 6 | 1 | 0 | 0 | 6 | 0 | 1 | 0 | 0 |

Experimental Results:

the experimental results showed that the effects of rLZ-8 on Dox-induced myocardial damage in mice were significant. The comparison between treatment group G and positive control group H showed that the treating effects of rLZ-8 were significant.

Embodiment 5: The Model Making of Renal Fibrosis of Mice 36 female Kunming mice weighed 18-22 g were selected and divided into 3 groups: respectively control group (PBS), model group 1 (CDDP 5 mg/kg), model group 2 (CDDP 7 mg/kg). The number of mice in each group was 12, 12 and 12. They were given intraperitoneal injections for 200 μl/per time/per mouse for 5 consecutive days, and the injection volumes contained the appropriate doses of cisplatin (CDDP). On the $1^{st}$, the $3^{rd}$, the $5^{th}$, the $7^{th}$, the $14^{th}$ and the $28^{th}$ days the mice were weighed and the statistics for the survival rates in each group were recorded.

Experimental Results:

We found that when the dose of cisplatin (CDDP) injection was 7 mg/kg, the mortality rate of mice was rather high and they were unable to survive. Starting from the $3^{rd}$ day, the mice began to die. On the $7^{th}$ day, the survival rate was 60%; on the $28^{th}$ day, only 30% of the mice survived. In the 5 mg/kg dose group, the mice were able to survive properly; on the $14^{th}$ day, the deaths of mice were discovered; on the $28^{th}$ day, the survival rate of the mice was 90%.

In the experiments we found that even the survival of the mice was guaranteed, due to kidney toxicity of cisplatin and its side effects on other organs, 5 mg/kg doses could lead to weight loss in mice, and 7 mg/kg cisplatin dose concentration seriously affected the normal survival of mice, so it was an inappropriate dose concentration to make models in this experiment. 5 mg/kg cisplatin dose concentration ensured the survival rates of the mice and caused weight loss of the mice; subsequent histological examination and molecular indexes were consistent with the known reports results. Therefore, 5 mg/kg cisplatin dose concentration was chosen as the concentration to make models in this experiment.

Embodiment 6: Treating Effects of rLZ-8 on Cisplatin (CDDP)-Induced Renal Damage in Mice Experiment Grouping and Treating Process:

30 female Kunming mice were randomly divided into 3 groups and were given the following treatment: the blank control group (group A), from the $1^{st}$ day, were given intraperitoneal injection of PBS for 5 consecutive days. The negative control group (group B), from the $1^{st}$ day, were given intraperitoneal injection of PBS for 5 consecutive days, and from the $7^{th}$ day to the $28^{th}$ day were given tail vein injection of PBS. The rLZ-8 treatment group (group C rLZ-8 123 μg/Kg), from the $1^{st}$ day, were I given intraperitoneal injection of 5 mg/kg cisplatin for 5 consecutive days; from the $7^{th}$ day to the $28^{th}$ day, 123 μg rLZ-8 were given by way of tail vein injection.

Experimental Testing Methods:

On the $14^{th}$ and the $28^{th}$ day, in each group two mice were selected and killed, and kidneys of the mice were taken out. The kidneys were fixed with 4% paraformaldehyde solution and the sections were embedded with paraffin. The grades of tissue damage and extracellular matrix (mainly collagen) deposition were assessed by Masson trichrome staining (MTS).

Figure 2:
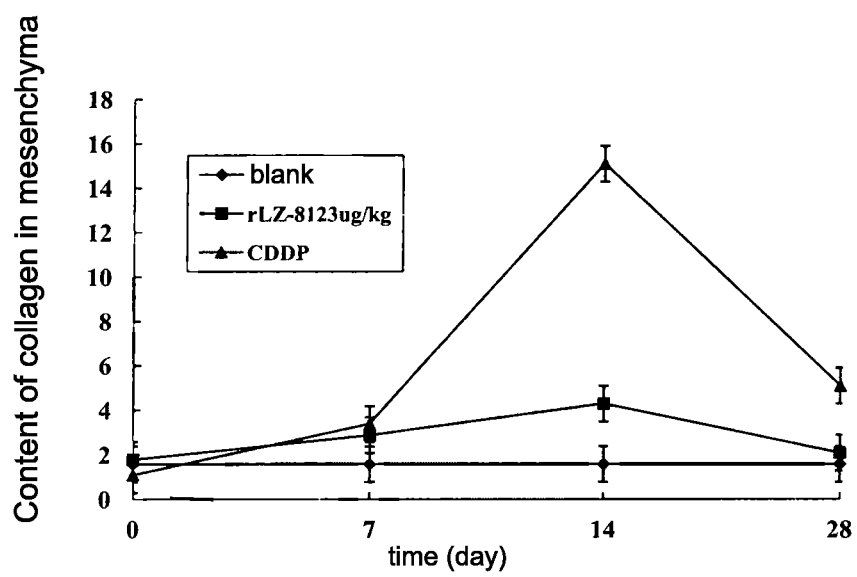
FIG. 2 shows influence of rLZ-8 on Mesenchyma collagen content of renal fibrosis.

Experimental Results:

The experimental results showed that rLZ-8 had some inhibitory effect on the increase of interstitial collagen matrix components in renal fibrosis. Results of MTS on kidney tissue sections showed that on the $14^{th}$ day, the grades of tissue damage in group C was lower than the CDDP group, and its matrix collagen content was also lower than the CDDP group; on the $28^{th}$ day, the grades of damage and atrophy of kidney structure increased, at the same time the content of the matrix of muscle fibers also increased. Compared with CDDP group, kidney damage in group C was inhibited or improved. Through Image-Pro Plus6.0 analysis (FIG. 1), on the $14^{th}$ day, compared with CDDP group, interstitial collagen deposition in group C was significantly inhibited; on the $28^{th}$ day, there was significant difference in the content of muscle fiber in matrix between rLZ-8 group and CDDP group (FIG. 2), which showed that rLZ-8 is capable of inhibiting collagen synthesis or promote collagen degradation.

Embodiment 7: Treating Effect of rLZ-8 on $CCl_4$-Induced Renal Fibrosis in Mice Experiment Grouping:

model group, positive drug group and the treatment group were given subcutaneous injection of 50% volume fraction carbon tetrachloride olive oil solution, twice a week, starting 8:00 in the morning on Mondays and Thursdays, lasting for 8 weeks to replicate the cirrhosis model. For the first time the dose was 0.5 ml/100 g in accordance with weights of the mice, then 0.3 ml/100 g every four days in accordance with weights of the mice. They ate and drank water freely. At the same time on Mondays changes in rats' weights were monitored and the possibility of liver failure was preliminary estimated in order to reduce the mortality rated caused by replicating the cirrhosis model.

Treating Process:

In the control group (group A), the model group (group B), the positive drug group (glycyrrhizin group C), the low-dose treatment group (group D), the medium-dose treatment group (group E) and the high-dose treatment group (group F), 8 weeks after the cirrhosis models were built, the rats were anesthetized with ether, blood was drawn from retinal venous plexus to test serum liver biochemical indicators; the positive drug group were given subcutaneous injection of Ganlixin solution, the injection volume was 12.5 mg/kg. The process was performed once a day, lasting for 4 weeks; for the low, medium and high rLZ-8 dose groups, the concentration of subcutaneous injections were 15 μg/kg, 30 μg/kg and 6 μg/kg respectively; the injections were given once a day for 4 weeks; till the end of the $12^{th}$ week, the mice were denied food but not water for 18 hours and anesthetized with ether. The eyeball blood of the rats was drawn, about 10 ml samples of blood were centrifuged to get serum and then were put into a −20° C. deep freezer to be tested for serum biochemical indexes.

Experimental Results:

Animal hepatic fibrosis models were copied. With aggravated liver cirrhosis of the rat, body mass of the rat was significantly reduced. Comparing the body mass of the rat among groups, the difference between the normal group and model group was statistically significant, P<0.05. The difference between the model group and the high-dose *Ganoderma Lucidum* Immunoregulation Protein group was statistically significant, P<0.05. The body mass in the control group increased more significantly, the model group had the lowest body mass. Compared with the model group, in the treatment group the body mass increased. The difference among the model group and high, medium and low dose prevention groups was not significant, P>0.05.

Due to the presence of portal hypertension caused by cirrhosis, liver weight increased. Statistics showed that liver weight was the highest in the model group, it was low in the normal group; compared with the model group, the liver weight in the treatment group decreased. The difference among groups was statistically significant, P<0.05. As can be seen from Table 7, the average liver weight in the control group was the lowest and the change range was small; the average liver weight in the model group was the highest and the change range was big; compared with the model group, the average liver weight in the control group decreased. The trends of change in liver indexes were similar, the control group was the lowest, the model group was the highest, and compared with the model group, the indexes in the treatment group decreased. Among all those groups, the most obvious effect was observed in the high-dose rLZ-8 group.

TABLE 7

The effects of rLZ-8 on the body mass, liver weight and liver indexes of model rats with liver fibrosis

| Groups | Group A | Group B | Group C | Group D | Group E | Group F |
|---|---|---|---|---|---|---|
| Model weight (g) | 445 ± 24.3* | 292.6 ± 35.3 | 303.5 ± 39.2*# | 317.7 ± 20.8*# | 296.5 ± 35.9*# | 301.1 ± 32.3*# |
| Final weights (g) | 482.6 ± 29.0* | 322.4 ± 39.3 | 397.1 ± 46.4*# | 402 ± 16.0*# | 387.7 ± 43.4*# | 395.4 ± 32.2*# |
| Liver weights (g) | 10.99 ± 2.11* | 13.947 ± 2.10 | 12.43 ± 2.25# | 13.04 ± 1.56* | 12.3 ± 1.74 | 12.15 ± 1.32# |
| Liver indexes (%) | 0.023 ± 0.004* | 0.043 ± 0.006 | 0.031 ± 0.004*# | 0.032 ± 0.003*# | 0.032 ± 0.007*# | 0.036 ± 0.008*# |

Compared with control group, *P < 0.05;
compared with model group, #P < 0.05.

In the present experiment, the rats' liver fibrosis models were replicated by $CCl_4$:olive oil (1:1) for 8 weeks. The AST enzyme and ALT enzyme activity of serum of the rat was significantly higher (P<0.05) compared with the normal control group, and the difference was statistically significant; compared with the control group, ALB content significantly decreased (P<0.05), the difference was statistically significant; when the model was successfully replicated, the rats were injected with different doses of rLZ-8, 10 days, 20 days and 30 days after drug administration, the AST enzyme activity, the ALT enzyme activity and the content of ALB were measured. The results showed that in the rLZ-8 treatment group, as the time of administration increased, rat serum AST enzyme and ALT enzyme activity gradually decreased, while ALB content gradually increased. Compared with the control group, the difference was obvious and was statistically significant. The effect of medium dose rLZ-8 was the best.

TABLE 8

The effects of rLZ-8 on the serum ALT (U/L), AST (U/L) and ALB (g/L) activity of model rats with liver fibrosis

| Groups | Day 10 | | | Day 20 | | | Day 30 | | |
|---|---|---|---|---|---|---|---|---|---|
| | ALT | AST | ALB | ALT | AST | ALB | ALT | AST | ALB |
| Group A | 23.0 ± 0.5* | 57.7 ± 3.4▲ | 39.8 ± 0.2# | 20.3 ± 0.6* | 91.0 ± 2.1▲ | 34.1 ± 0.2# | 16.0 ± 0.4* | 52.2 ± 1.5▲ | 35.2 ± 0.1# |
| Group B | 231.9 ± 1.8 | 333.0 ± 7.8 | 34.1 ± 0.1 | 191.9 ± 3.1 | 329.2 ± 14.5 | 29.2 ± 0.2 | 134.6 ± 1.6 | 346.3 ± 7.1 | 31 ± 0.2 |
| Group C | 143.3 ± 0.9* | 176.2 ± 6.1▲ | 34.8 ± 0.2# | 126.2 ± 1.3* | 205.8 ± 4.2▲ | 30.0 ± 0.2# | 49.5 ± 0.6* | 59.0 ± 1.9▲ | 32.5 ± 0.1# |
| D组 | 130.2 ± 0.3* | 133.8 ± 7.3▲ | 36.1 ± 0.1# | 121.2 ± 0.3* | 145.5 ± 0.8▲ | 30.6 ± 0.1# | 39.3 ± 0.2* | 61.5 ± 0.3▲ | 33.1 ± 0.1# |

TABLE 8-continued

The effects of rLZ-8 on the serum ALT (U/L), AST (U/L) and ALB (g/L) activity of model rats with liver fibrosis

| Groups | Day 10 | | | Day 20 | | | Day 30 | | |
|---|---|---|---|---|---|---|---|---|---|
| | ALT | AST | ALB | ALT | AST | ALB | ALT | AST | ALB |
| E组 | 83.9 ± 0.2* | 111.5 ± 3.7▲ | 36.6 ± 0.2# | 67.8 ± 0.1* | 120.4 ± 0.3▲ | 31.8 ± 0.1# | 37.0 ± 0.1* | 53.8 ± 0.2▲ | 33.9 ± 0.2# |
| F组 | 92.6 ± 0.4* | 123.9 ± 4.9▲ | 35.8 ± 0.1# | 71.3 ± 0.2* | 221.7 ± 0.6▲ | 31.3 ± 0.2# | 38.2 ± 0.2* | 60.3 ± 0.6▲ | 33.2 ± 0.1# |

Note:
*▲#means compared with the model group, the ALT, AST, ALB $p < 0.05$ respectively.

What is claimed is:

1. A method for treatment of the tissue fibrosis induced by any reason or diseases via applying a therapeutically effective amount of *Ganoderma lucidum* immunoregulation protein (rLZ-8), wherein the therapeutically effective amount of *Ganoderma lucidum* immunoregulation protein (rLZ-8) further comprises a medicinally acceptable amount of adjuvant.

2. A method for treatment of the tissue fibrosis induced by any reason or diseases via applying a therapeutically effective amount of *Ganoderma lucidum* immunoregulation protein (rLZ-8), wherein an administration of *Ganoderma lucidum* immunoregulation protein (rLZ-8) for treatment is by oral or parenteral route; *Ganoderma lucidum* immunoregulation protein (rLZ-8) for treatment is prepared as oral solution, tablets, pills, capsules or other forms for oral administration; and externally applied *Ganoderma lucidum* immunoregulation protein (rLZ-8) as injections or other forms for parenteral route.

* * * * *